United States Patent [19]

Felcht

[11] 4,329,303

[45] May 11, 1982

[54] PROCESS FOR THE PREPARATION OF 1-OXO-PHOSPHOLANE-CHLORO-HYDRINS

[75] Inventor: Utz-Hellmuth Felcht, Bruchmühlbach, Fed. Rep. of Germany

[73] Assignee: Hoechst Aktiengesellschaft, Frankfurt am Main, Fed. Rep. of Germany

[21] Appl. No.: 167,014

[22] Filed: Jul. 9, 1980

[30] Foreign Application Priority Data

Jul. 11, 1979 [DE]  Fed. Rep. of Germany ....... 2927916

[51] Int. Cl.$^3$ ............................ C07F 9/32; C07F 9/53
[52] U.S. Cl. .................................. 260/986; 260/936; 568/12
[58] Field of Search ................... 260/936, 986; 568/12

[56] References Cited

U.S. PATENT DOCUMENTS

| | | |
|---|---|---|
| 2,887,498 | 5/1959 | Hearne et al. |
| 3,183,250 | 5/1965 | Rosenblatt et al. |
| 4,052,484 | 10/1977 | Schliebs et al. ........................ 568/12 |
| 4,080,385 | 3/1978 | Block ................................. 260/936 |
| 4,102,949 | 7/1978 | Schliebs ............................. 260/936 |

FOREIGN PATENT DOCUMENTS

| | | | |
|---|---|---|---|
| EP 22546 | 1/1981 | European Pat. Off. | ............. 568/12 |
| 225187 | 8/1968 | U.S.S.R. | ............................. 260/936 |

OTHER PUBLICATIONS

Houben-Weyl, Band V/3, (1962) pp. 768-771.
Weissberger, Heterocyclic Compounds with Three-Space and Four-Membered Rings, Part 1 (1964), pp. 95-97.
Arbuzov et al., Izv. Aked. Nauk. SSSR 1968, pp. 1237 et seq.

*Primary Examiner*—Anton H. Sutto
*Attorney, Agent, or Firm*—Curtis, Morris & Safford

[57] ABSTRACT

1-Oxo-phospholane-chlorohydrins are prepared by reacting 1-oxo-phospholenes with chlorine in the presence of bases which bond hydrogen chloride in a molar ratio of about 1:1:1 in water; the water is optionally in mixture with a water-miscible inert organic solvent. Most of the reaction products are new compounds, which are chiefly used as intermediate products in the field of plastics, of hydraulic fluids and of catalysts for converting isocyanates into carbodiimides.

9 Claims, No Drawings

PROCESS FOR THE PREPARATION OF 1-OXO-PHOSPHOLANE-CHLORO-HYDRINS

The 1-oxo-phospholane-chlorohydrins to which this Application relates are isomeric compounds of the formulae Ia and Ib:

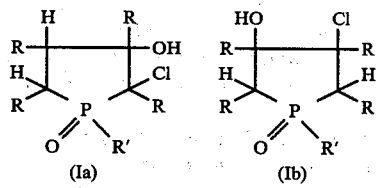

wherein the radicals R, which can be identical or different, denote hydrogen, organic radicals and/or halogen and R' denotes an organic radical or an organic radical which is bonded via oxygen.

The compounds are intermediate products in various fields.

Of 1-oxo-phospholane-chlorohydrins of the formulae Ia and Ib, only 3-chloro-3,4-dimethyl-4-hydroxy-1-phenyl-1-oxo-phospholane has been known hitherto [Soviet Union Patent No. 225,187; B. A. Arbuzov, A. P. Rakov and A. O. Vizel, Izv. Akad.Nauk. SSSR (English translation) 1969, 2,079]; the compound has the formula II:

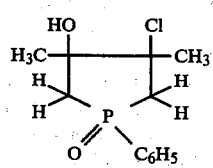

It is prepared in 80% yield by opening the ring of the corresponding 3,4-epoxy-1-oxo-phospholane in ether with dry hydrogen chloride. The 3,4-dimethyl-3,4-epoxy-1-phenyl-1-oxo-phospholane required for this reaction is first prepared in 74% yield from 3,4-dimethyl-1-phenyl-1-oxo-$\Delta^3$-phospholene and peracetic acid [compare B. A. Arbuzov, A. P. Rakov, A. O. Vizel, L. A. Shapshinskaya and N. P. Kulikova, Izv. Akad.Nauk. SSSR (English translation) 1968 1,237]. The two stages of the reaction can be represented by the following equations (compare equations 1a and 1b):

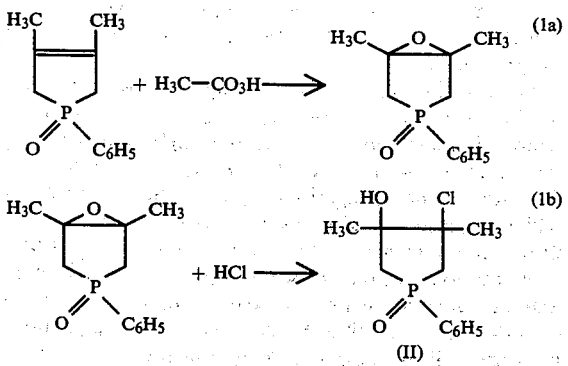

However, for an industrial procedure and an extension beyond the special case of the preparation of II, the two-stage synthesis is expensive and not sufficiently economical, since, on the one hand, a yield of only 59% is achieved, relative to the starting 1-oxo-$\Delta^3$-phospholene, and, on the other hand, the process is a two-stage synthesis, which is associated with considerable expenditure of time and materials.

It was thus desirable, and an object of the present invention, to develop a simpler and more economical process which, as well as being applicable to the preparation of the known 1-oxo-phospholane-chlorohydrin II, can also be used for the preparation of other 1-oxo-phospholane-chlorohydrins which are new.

According to the invention, this object is achieved in a simple and satisfactory manner, starting from 1-oxo-phospholenes, by reacting 1-oxo-phospholenes with chlorine in the presence of bases which bond hydrogen chloride in a molar ratio of 1:1:1 in water; the water is optionally in mixture with a water-miscible inert organic solvent.

The reaction of olefins with chlorine and water to give 1,2-chlorohydrins is known in principle (compare R. Stroh in: Houben-Weyl, Methoden der org. Chemie (Methods of organic Chemistry), G. Thieme Verlag Stuttgart, 1962, volume V/3, page 768 et seq.), but the reaction frequently proceeds with simultaneous formation of 1,2-dichloro compounds as competing products (compare R. Stroh, ibid. page 771).

It was thus exceptionally surprising that high to almost quantitative yields of the desired 1-oxo-phospholane-chlorohydrins are obtained in the process according to the invention without formation of corresponding 1-oxo-phospholane-2,3- or -3,4-dichloro products being observed. This fact is all the more surprising since, as experiments performed by Farbwerke Hoechst Aktiengesellschaft have shown, the corresponding reaction of 1-oxo-phospholenes with bromine (instead of chlorine) leads exclusively to 1-oxo-2,3- and -3,4-dibromophospholanes and to virtually no bromohydrins.

It was furthermore surprising that when those 1-oxo-phospholenes which carry an alkoxy group as a substitutent on the phosphorus are used as starting materials, the phosphinic acid ester function thus present is not split under the experimental conditions in aqueous-acid solution.

Finally, the smooth formation of 1-oxo-phospholane-chlorohydrins from 1-oxo-phospholenes, chlorine and water in the manner according to the invention was also exceptionally surprising because it is known (compare German Auslegeschrift 2,245,634 and K. Sasse in Houben-Weyl, Methoden der org. Chemie (Methods of organic Chemistry), G. Thieme Verlag Stuttgart, 1963, volume XII/1, page 127) that phosphine oxides form very stable salts with acids such as are formed when chlorine is passed into water (HCl and HOCl).

Starting substances which can be used for the process according to the invention are in principle all the possible 1-oxo-phospholenes with the double bond in the $\Delta^2$- or $\Delta^3$-position of the P-containing 5-membered ring and with an organic radical, or an organic radical bonded via oxygen, on the phosphorus; however, it is preferable to use the 1-oxo-phospholenes falling under the formulae IIIa and IIIb:

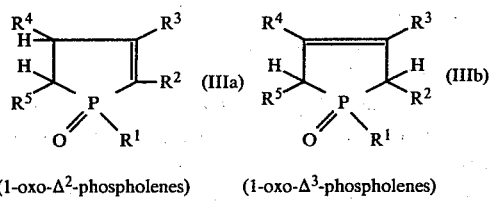

(1-oxo-Δ²-phospholenes)  (1-oxo-Δ³-phospholenes)

wherein $R^1$ is $(C_1-C_{12})$-alkyl, optionally substituted by Cl and/or Br, $(C_1-C_{12})$-alkoxy, optionally substituted by Cl and/or Br, or cyclopentyl, cyclohexyl, phenyl, naphthyl, cyclopentoxy, cyclohexoxy, phenoxy or naphthoxy, optionally substituted by $(C_1-C_4)$-alkyl, $(C_1-C_4)$-alkoxy, Cl and/or Br, and $R^2$, $R^3$, $R^4$ and $R^5$ independently of one another are H, $(C_1-C_4)$-alkyl, $(C_1-C_4)$-alkoxy, phenyl, Cl or Br.

Particularly preferred starting substances are those 1-oxo-phospholenes of the formulae IIIa and IIIb, in which $R^1$ is $(C_1-C_4)$-alkyl, optionally substituted by Cl and/or Br, $(C_1-C_4)$-alkoxy, optionally substituted by Cl and/or Br, or phenyl, $R^2$ and $R^5$ are identical and are H and $R^3$ and $R^4$ independently of one another are H or $CH_3$.

If the groups mentioned for $R^1$ are further substituted, they are preferably monosubstituted.

Concrete examples of 1-oxo-phospholenes falling under the formulae IIIa and IIIb which may be mentioned are: 1-methyl-1-oxo-Δ²(Δ³)-phospholene, 1-ethyl-1-oxo-Δ²(Δ³)-phospholene, 1-propyl-1-oxo-Δ²(Δ³)-phospholene, 1-butyl-1-oxo-Δ²(Δ³)-phospholene, 1-phenyl-1-oxo-Δ²(Δ³)-phospholene, 1-chloromethyl-1-oxo-Δ²(Δ³)-phospholene, 1,3-dimethyl-1-oxo-Δ²(Δ³)-phospholene, 1-ethyl-3-methyl-1-oxo-Δ²(Δ³)-phospholene, 3-methyl-1-phenyl-1-oxo-Δ²(Δ³)-phospholene, 1,3,4-trimethyl-1-oxo-Δ²(Δ³)-phospholene, 1-ethyl-3,4-dimethyl-1-oxo-Δ²(Δ³)-phospholene, 3,4-dimethyl-1-phenyl-1-oxo-Δ²(Δ³)-phospholene, 1methoxy-1-oxo-Δ²(Δ³)-phospholene, 1-ethoxy-1-oxo-Δ²(Δ³)-phospholene, 1-butoxy-1-oxo-Δ²(Δ³)-phospholene, 1phenoxy-1-oxo-Δ²(Δ³)-phospholene, 1-β-chloroethoxy-1-oxo-Δ²(Δ³)-phospholene and the like. They are accessible by known processes (K. Sasse in: Houben-Weyl, Methoden der org. Chemie (Methods of organic Chemistry), G. Thieme Verlag Stuttgart 1963, volume XII/1, page 138 et seq.; German Auslegeschrift 2,036,173; and K. Hasserodt, K. Hunger and F. Korte, Tetrahedron 1963, 1,563).

It is, of course, also possible to employ a mixture of the Δ²- and Δ³-isomeric 1-oxo-phospholenes; the process according to the invention then gives a mixture of the corresponding 2-chloro-3-hydroxy- and 3-chloro-4-hydroxy-1-oxo-phospholanes. The use of a mixture of the Δ²- and Δ³-isomeric 1-oxo-phospholenes is suitable, above all, when such an isomer mixture has already been formed in the process used for the preparation of the 1-oxo-phospholenes (compare, for example, German Pat. No. 1,192,204 and German Auslegeschrift No. 2,036,173), and when the mixture of isomeric 1-oxo-phospholane-chlorohydrins now formed therefrom can be further used as such or can be separated without particular effort.

Gaseous chlorine is preferably used as the source of chlorine, but an aqueous solution of chlorine, for example, can also be employed.

Suitable bases which bond hydrogen chloride are virtually all the basic substances customary for such a purpose; alkali metal hydroxides, carbonates and bicarbonates, ammonia and/or lower aliphatic amines are preferably used. Sodium hydroxide, potassium hydroxide, sodium carbonate, potassium carbonate, sodium bicarbonate, ammonia, ethylamine, diethylamine, triethylamine, di-i-proplyamine, n-butylamine and the like are particularly preferred.

Suitable water-miscible, inert (towards the starting compounds and end compounds) organic solvents are preferably lower, i.e., $(C_1-C_4)$-alcohols, lower aliphatic ketones and/or water-soluble ethers, for example methanol, ethanol, n- and i-propanol, acetone, dioxan and the like.

The process according to the invention can be carried out within a relatively wide temperature range. In general, it is carried out in the temperature range from about $-10°$ to $+100°$ C.; a temperature range between about 0° and 50° C. is preferred.

The reaction time is on average a few minutes. The reaction in general proceeds spontaneously with slight warming. External cooling can be used, but is not absolutely necessary.

The ratio between the solvent and the sum of the reactants can be varied within a relatively wide range. In general, a weight ratio of about 1:1 to about 20:1 (solvent to the sum of the reactants), preferably a ratio of about 2:1 to about 4:1, is used.

In general, a procedure is followed, for example, in which a solution of one or more reactants is initially introduced into the reaction vessel and the remaining components are added dropwise, simultaneously or successively. Preferably, the 1-oxo-phospholene is initially introduced in water or a mixture of water and one of the water-miscible inert organic solvents mentioned, and chlorine and the base which bonds hydrogen chloride are added simultaneously; the addition of chlorine and base is particularly preferably carried out in a manner such that a pH of about 2 to 9 is always maintained in the reaction solution. In an individual case, however, another sequence for the addition of the components may of course be expedient and is thus possible.

It is expedient to employ the reactants 1-oxo-phospholene, chlorine and base which bonds hydrogen chloride in a molar ratio of about 1:1:1, but any of the reactants can also be present in excess. The 4th reactant, that is to say water, is in general used in excess, since it is also employed as the solvent, with or without an appropriate inert organic solvent. When the reaction has ended, it is furthermore expedient to neutralize the reaction solution.

The reaction batch is worked up by known methods. In the case of water-soluble products, the solvent is removed under reduced pressure or under normal pressure and the residue is freed from the salt precipitate by filtration or centrifugation. In the case of products which separate out directly from the reaction mixture, filtration, under normal pressure or increased pressure, or extraction with a suitable organic solvent is in general carried out. After removal of the solvent, the 1-oxo-phospholane-chlorohydrins then crystallize out in a pure form. In some cases, structural isomers of 1-oxo-phospholane-chlorohydrins are also formed when carrying out the process according to the invention; it is possible, if desired, to isolate these isomers separately from the reaction mixture on the basis of their different properties, such as different solubility and the like (compare, for example, Examples 9 and 19).

Further purification is in itself unnecessary, but if desired, can be carried out by known methods (recrystallization, reprecipitation and the like). Compared with the abovementioned procedure of B. A. Arkuzov et al, loc. cit., the process according to the invention is simpler and more economical, since it permits, starting from 1-oxo-phospholenes, the preparation of the corresponding 1-oxo-phospholane-chlorohydrins in excellent yields in a one-stage process without isolation of an intermediate stage and without appreciable effort. Furthermore, the process also enables a number of new compounds to be prepared.

When 1-oxo-phospholenes of the formulae IIIa and IIIb are used as starting materials, the process can be represented by formulae as follows (equations 2a and 2b; B=base):

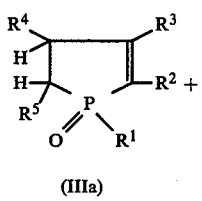

(IIIa)

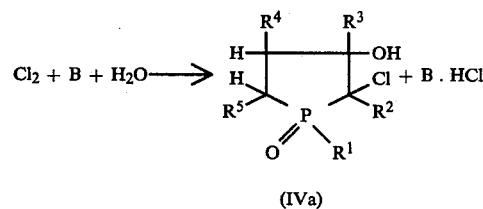

(IVa)

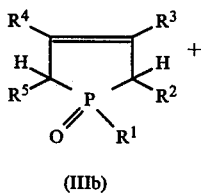

(IIIb)

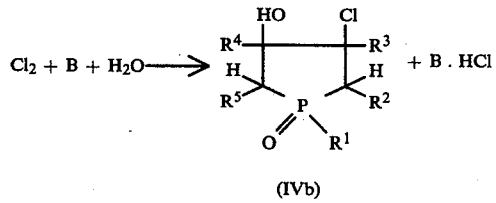

(IVb)

In the formulae, the radicals $R^1$–$R^5$ have the meaning given the first time formulae IIIa and IIIb occurred. The 1-oxo-phospholane-chlorohydrins IVa and IVb are new, with the exception of the case where $R^1$ is $C_6H_5$, $R^2$ and $R^5$ are identical and are H and $R^3$ and $R^4$ are identical and are $CH_3$.

Preferred new compounds IVa and IVb are those in which $R^1$ is $(C_1$–$C_4)$-alkyl, optionally substituted—preferably monosubstituted—by Cl and/or Br, or $(C_1$–$C_4)$-alkoxy, optionally substituted—preferably monosubstituted—by Cl and/or Br, $R^2$ and $R^5$ are identical and are H and $R^3$ and $R^4$ independently of one another are H or $CH_3$, and those in which $R^1$ is $C_6H_5$ and $R^2$, $R^3$, $R^4$ and $R^5$ are H.

The compounds are valuable intermediate products for the preparation of 2,3and 3,4-epoxy-1-oxo-phospholanes. They can be converted into these epoxy compounds by the methods known for the preparation of epoxides from 1,2-chlorohydrins (by means of bases); compare, for example, G. Dittus in Houben-Weyl, Methoden der org. Chemie (Methods of organic Chemistry), G. Thieme Verlag Stuttgart 1965, volume VI/3, page 374 et seq.

As is known for other phosphorus-containing epoxides these epoxy compounds are used, inter alia, as copolymers which are stable to heat (U.S. Pat. No. 2,770,610), as hydraulic fluids (U.S. Pat. No. 2,826,592), as additives to vinyl polymers (U.S. Pat. No. 2,956,369) etc. The 3,4-expoxy-1-oxo-phospholanes, in particular, are also important intermediate products for the preparation of the corresponding 3,4-dihydroxy-1-oxo-phospholanes, which, when incorporated into polymers, are of industrial and economic importance as effective catalysts for converting isocyanates into carbodiimides (German Offenlegungschrift No. 2,602,646).

The invention will now be illustrated further with the aid of the following examples.

EXAMPLE 1

71.0 g (1.0 mole) of chlorine are passed into a solution of 116 g (1.0 mole) of 1-methyl-1-oxo-$\Delta^3$-phospholene in 300 ml of water at 20°–25° C., with external cooling. At the same time, a solution of 53 g (0.5 mole) of sodium carbonate in 150 ml of water is added dropwise in a manner such that the pH value of the reaction mixture always remains between 4 and 8. The mixture is then neutralized, water is stripped off at 40° C./$1.6 \times 10^{-2}$ bar and the residue is stirred with 150 ml of methylene chloride. The salt which has precipitated is filtered off and the solvent is removed from the filtrate at 30° C./$2.0 \times 10^{-2}$ bar to give 166 g (98.5%) of 3-chloro-4-hydroxy-1-methyl-1-oxo-phospholane as colorless crystals of melting point 134°–136° C. (recrystallized from acetone).

$C_5H_{10}ClO_2P$ (168.56)

| calculated: | C 35.63 | H 5.98 | Cl 21.03 | P 18.38 |
|---|---|---|---|---|
| found: | C 35.6 | H 5.8 | Cl 21.0 | P 18.6 |

EXAMPLE 2

Example 1 is repeated, but the sodium carbonate solution is added after the chlorine has been passed in. Working up then gives 85 g (50.4%) of 3-chloro-4-hydroxy-1-methyl-1-oxo-phospholane.

EXAMPLE 3

Example 1 is repeated, but the sodium carbonate solution is added before the chlorine is passed in. Working up then gives 114 g (67.6%) of 3-chloro-4-hydroxy-1-methyl-1-oxo-phospholane.

Comparison of Examples 1 to 3 shows that the yield of 3-chloro-4-hydroxy-1-methyl-1-oxo-phospholane can be increased by maintaining a certain pH range in the reaction mixture, but the sequence in which the components are added is in principle not critical for the process according to the invention.

EXAMPLE 4

Example 1 is repeated, but instead of sodium carbonate, 40 g (1.0 mole) of sodium hydroxide are used. Working up then gives 158 g (93.7%) of 3-chloro-4-hydroxy-1-methyl-1-oxo-phospholane.

Comparison of Example 1 with Example 4 shows that the nature of the base used is not critical in the process according to the invention.

EXAMPLE 5

Example 1 is repeated, but external cooling is omitted. The reaction temperature then rises up to 45° C. Working up gives 162 g (96.1%) of 3-chloro-4-hydroxy-1-methyl-1-oxo-phospholane.

Comparison of Example 1 with Example 5 shows that the temperature of the reaction mixture is not critical for the process according to the invention.

EXAMPLE 6

35.5 g (0.5 mole) of chlorine are passed into a solution of 65 g (0.5 mole) of 1,3-dimethyl-1-oxo-$\Delta^3$-phospholene in 150 ml of water at 20°–25° C., with external cooling. At the same time, a solution of 26.5 g (0.25 mole) of sodium carbonate in 100 ml of water is added dropwise in a manner such that the pH value of the reaction mixture always remains between 4 and 8. The mixture is then neutralized, water is stripped off at 40° C./1.6×10$^{-2}$ bar and the residue is stirred with 100 ml of methylene chloride. The salt which has precipitated is filtered off and the solvent is removed from the filtrate at 30° C./2.0×10$^{-2}$ bar to give 89 g (97.5%) of 3-chloro-1,4-dimethyl-4-hydroxy-1-oxo-phospholane as colorless crystals of melting point 126°–127° C. (recrystallized from ethyl acetate).

$C_6H_{12}ClO_2P$ (182.59)

| calculated: | C 39.47 | H 6.62 | Cl 19.42 | P 16.96 |
|---|---|---|---|---|
| found: | C 39.7 | H 6.4 | Cl 19.6 | P 17.0. |

EXAMPLE 7

35.5 g (0.5 mole) of chlorine are passed into a solution of 89 g (0.5 mole) of 1-phenyl-1-oxo-$\Delta^3$-phospholene in 150 ml of water at 20°–25° C., with external cooling. At the same time, a solution of 26.5 g (0.25 mole) of sodium carbonate in 100 ml of water is added dropwise in a manner such that the pH value of the reaction mixture always remains between 4 and 8. The mixture is then neutralized, water is stripped off at 40° C./1.6×10$^{-2}$ bar and the residue is stirred with 100 ml of methylene chloride. The salt which has precipitated is filtered off and the solvent is removed from the filtrate at 30° C./2.0×10$^{-2}$ bar to give 99 g (85.9%) of 3-chloro-4-hydroxy-1-phenyl-1-oxo-phospholane as colorless crystals of melting point 138° C. (recrystallized from acetonitrile).

$C_{10}H_{12}ClO_2P$ (230.63)

| calculated: | C 52.08 | H 5.24 | Cl 15.37 | P 13.43 |
|---|---|---|---|---|
| found: | C 51.8 | H 5.1 | Cl 15.6 | P 13.5 |

EXAMPLE 8

35.5 g (0.5 mole) of chlorine are passed into a solution of 103 g (0.5 mole) of 3,4-dimethyl-1-phenyl-1-oxo-$\Delta^3$-phospholene in 150 ml of water at 20°–25° C., with external cooling. At the same time, a solution of 26.5 g (0.25 mole) of sodium carbonate in 100 ml of water is added dropwise in a manner such that the pH value of the reaction mixture always remains between 5 and 7. The mixture is then neutralized and the product which has precipitated is filtered off. Yield: 119 g (92%) of 3-chloro-3,4-dimethyl-4-hydroxy-1-phenyl-oxo-phospholane as colorless crystals of melting point 176° C. (recrystallized from dioxan).

$C_{12}H_{16}ClO_2P$ (258.69)

| calculated: | C 55.72 | H 6.23 | Cl 13.70 | P 11.97 |
|---|---|---|---|---|
| found: | C 55.7 | H 6.0 | Cl 13.6 | P 12.1 |

EXAMPLE 9

35.5 g (0.5 mole) of chlorine are passed into a solution of 96 g (0.5 mole) of 3-methyl-1-phenyl-1-oxo-$\Delta^3$-phospholene in 150 ml of water at 20°–25° C., with external cooling. At the same time, a solution of 26.5 g (0.25 mole) of sodium carbonate in 100 ml of water is added dropwise in a manner such that the pH value of the reaction mixture always remains between 4 and 7. The mixture is then neutralized, water is stripped off at 40° C./1.6×10$^{-2}$ bar and the residue is stirred with 100 ml of methylene chloride. The salt which has precipitated is filtered off and the solvent is removed from the filtrate at 30° C./2.0×10$^{-2}$ bar to give 117 g (95.7%) of an isomer mixture of 3-chloro-4-hydroxy-4-methyl-1-phenyl-1-oxo-phospholanes. Stirring the mixture with 100 ml of ethyl acetate and filtration gives one isomer as colorless crystals of melting point 174°–175° C. (recrystallized from propan-2-ol).

$C_{11}H_{12}ClO_2P$ (244.66)

| calculated: | C 54.00 | H 5.77 | Cl 14.49 | P 12.66 |
|---|---|---|---|---|
| found: | C 53.7 | H 5.5 | Cl 14.4 | P 12.7 |

Evaporation of the filtrate at 30° C./2.0×10$^{-2}$ bar, trituration of the residue with 50 ml of ether and filtration gives the other isomer as colorless crystals of melting point 134° C. (recrystallized from ethyl acetate/ether 1:2).

$C_{11}H_{12}ClO_2P$ (244.66)

| calculated: | C 54.00 | H 5.77 | Cl 14.49 | P 12.66 |
|---|---|---|---|---|
| found: | C 53.9 | H 5.6 | Cl 14.3 | P 12.6 |

EXAMPLE 10

Analogously to Example 9, 96 g (0.5 mole) of 3-methyl-1-phenyl-1-oxo-$\Delta^2$-phospholene in 150 ml of water are reacted with 35.5 g (0.5 mole) of chlorine and 26.5 g (0.25 mole) of sodium carbonate in 100 ml of water and the mixture is worked up. Working up gives 118 g (96.5%) of 2-chloro-3-hydroxy-3-methyl-1-phenyl-1-oxo-phospholane as colorless crystals of melting point 173° C. (recrystallized from propan-2-ol).

$C_{11}H_{12}ClO_2P$ (244.66)

| calculated: | C 54.00 | H 5.77 | Cl 14.49 | P 12.66 |
|---|---|---|---|---|
| found: | C 53.6 | H 5.8 | Cl 14.7 | P 12.7 |

Comparison of Example 9 with Example 10 shows that 1-oxo-$\Delta^2$- and 1-oxo-$\Delta^3$-phospholenes can be employed in the process according to the invention in the same manner (for use of mixtures of the two isomers, see Examples 14 and 15).

EXAMPLE 11

Analogously to Example 6, 66 g (0.5 mole) of 1-methoxy-1-oxo-$\Delta^3$-phospholene in 150 ml of water are reacted with 35.5 g (0.5 mole) of chlorine and 26.5 g (0.25 mole) of sodium carbonate in 100 ml of water and the mixture is worked up. Working up gives 91 g (98.6%) of 3-chloro-4-hydroxy-1-methoxy-1-oxo-phospholane as a colorless oil, which crystallizes completely after standing for a relatively long time. When recrystallization from ethyl acetate, colorless crystals of melting point 82° C. are obtained.

$C_5H_{10}ClO_3P$ (184.56)

| calculated: | C 32.54 | H 5.46 | Cl 19.21 | P 16.78 |
|---|---|---|---|---|
| found: | C 32.2 | H 5.4 | Cl 19.4 | P 16.3 |

EXAMPLE 12

Analogously to Example 6, 73 g (0.5 mole) of 1-ethoxy-1-oxo-$\Delta^3$-phospholene in 150 ml of water are reacted with 35.5 g (0.5 mole) of chlorine and 26.5 g (0.25 mole) of sodium carbonate in 100 ml of water and the mixture is worked up. Working up gives 95 g (95.7%) of 1-ethoxy-3-chloro-4-hydroxy-1-oxo-phospholane as colorless crystals of melting point 98° C. (recrystallized from ether at −70° C.).

$C_6H_{12}ClO_3P$ (198.59)

| calculated: | C 36.29 | H 6.09 | Cl 17.58 | P 15.60 |
|---|---|---|---|---|
| found: | C 36.1 | H 5.9 | Cl 17.9 | P 15.3 |

EXAMPLE 13

Example 12 is repeated, but 200 ml of a 1:1 mixture of water and ethanol are used as the solvent. Working up then gives 96 g (96.7%) of 1-ethoxy-3-chloro-4-hydroxy-1-oxo-phospholane.

Comparison of Example 12 with Example 13 shows that mixtures of water and suitable organic solvents can also be employed in the process according to the invention without the yield of 1-ethoxy-3-chloro-4-hydroxy-1-oxo-phospholane being reduced.

EXAMPLE 14

Analogously to Example 6, 80 g (0.5 mole) of 1-i-propoxy-1-oxo-$\Delta^3$-phospholene in 150 ml of water are reacted with 35.5 g (0.5 mole) of chlorine and 26.5 g (0.25 mole) of sodium carbonate in 100 ml of water and the mixture is worked up. Working up gives 98 g (92.2%) of 3-chloro-4-hydroxy-1-i-propoxy-1-oxo-phospholane as colorless crystals of melting point 104°–106° C. (recrystallized from ether at −70° C.).

$C_7H_{14}ClO_3P$ (212.62)

| calculated: | C 39.55 | H 6.64 | Cl 16.68 | P 14.57 |
|---|---|---|---|---|
| found: | C 39.3 | H 6.8 | Cl 17.0 | P 14.6 |

EXAMPLE 15

Example 14 is repeated, but instead of the isomerically pure 1-i-propoxy-1-oxo-$\Delta^3$-phospholene, 80 g (0.5 mole) of a mixture of 60.9% of 1-i-propoxy-1-oxo-$\Delta^3$- and 39.1% of 1-i-propoxy-1-oxo-$\Delta^2$-phospholene are reacted. Working up then gives 104 g (97.8%) of a mixture of 3-chloro-4-hydroxy- and 2-chloro-3-hydroxy-1-i-propxy-1-oxo-phospholane as a colorless oil which solidifies.

$C_7H_{14}ClO_3P$ (212.62)

| calculated: | C 39.55 | H 6.64 | Cl 16.68 | P 14.57 |
|---|---|---|---|---|
| found: | C 39.0 | H 6.5 | Cl 16.7 | P 14.2 |

Comparison of Example 14 with Example 15 shows that the process according to the invention can also be carried out with mixtures of isomeric $\Delta^2$- and $\Delta^3$-phospholenes. Mixtures of 3-chloro-4-hydroxy- and 2-chloro-3-hydroxy-1-oxo-phospholanes are then obtained.

EXAMPLE 16

35.5 g (0.5 mole) of chlorine are passed into a solution of 90.3 g (0.5 mole) of 1-$\beta$-chloroethoxy-1-oxo-$\Delta^3$-phospholene in 150 ml of water, with external cooling. At the same time, a solution of 26.5 g (0.25 mole) of sodium carbonate in 100 ml of water is added dropwise in a manner such that the pH value of the reaction mixture always remains between 6 and 7. The oil formed is then separated off, the aqueous phase is extracted 3 times with 50 ml of methylene chloride each time, the oil which has been separated off is combined with the organic extracts and the mixture is dried over sodium sulfate. The drying agent is filtered off and the solvent is removed from the filtrate at 30° C./2.0×10$^{-2}$ bar to give 99 g (85.0%) of 3-chloro-1-$\beta$-chloroethoxy-4-hydroxy-1-oxo-phospholane as a colorless oil, which solidifies when left to stand for a relatively long period.

$C_6H_{11}Cl_2O_3P$ (233.03)

| calculated: | C 30.93 | H 4.76 | Cl 30.43 | P 13.29 |
|---|---|---|---|---|
| found: | C 30.9 | H 4.7 | Cl 30.8 | P 13.0 |

EXAMPLE 17

Analogously to Example 16, 80 g (0.5 mole) of 1-ethoxy-3-methyl-1-oxo-$\Delta^3$-phospholene in 150 ml of water are reacted with 35.5 g (0.5 mole) of chlorine and 26.5 g (0.25 mole) of sodium carbonate in 100 ml of water and the mixture is worked up. Working up gives 104 g (97.9%) of 1-ethoxy-3-chloro-4-hydroxy-4-methyl-1-oxo-phospholane as colorless crystals of melting point 105° C. (recrystallized from ether at −70° C.).

$C_7H_{14}ClO_3P$ (212.62)

| calculated: | C 39.55 | H 6.64 | Cl 16.68 | P 14.57 |
|---|---|---|---|---|
| found: | C 39.5 | H 6.6 | Cl 17.0 | P 14.6 |

EXAMPLE 18

Analogously to Example 17, 80 g (0.5 mole) of 1-ethoxy-3-methyl-1-oxo-$\Delta^2$-phospholene in 150 ml of water are reacted with 35.5 g (0.5 mole) of chlorine and 26.5 g (0.25 mole) of sodium carbonate in 100 ml of water and the mixture is worked up. Working up gives 104 g (97.9%) of 1-ethoxy-2-chloro-3-hydroxy-3-methyl-1-oxo-phospholane as a colorless oil of boiling point 172° C./1.33×10$^{-5}$ bar.

$C_7H_{14}ClO_3P$ (212.62)

| calculated: | C 39.55 | H 6.64 | Cl 16.68 | P 14.57 |
|---|---|---|---|---|

| -continued | | | |
|---|---|---|---|
| found: | C 39.2 H 6.3 | Cl 17.1 | P 14.2 |

For the comparison of Example 17 with Example 18, see the remarks in Example 10.

EXAMPLE 19 35.5 g (0.5 mole) of chlorine are passed into a solution of 80 g (0.5 mole) of 3,4-dimethyl-1-methoxy-1-oxo-Δ³-phospholene in 150 ml of water, with external cooling. At the same time, a solution of 26.5 g (0.25 mole) of sodium carbonate in 100 ml of water is added dropwise in a manner such that the pH value of the solution always remains between 5 and 7. Filtration gives 48 g (45.2%) of one isomer of 3-chloro-3,4-dimethyl-4-hydroxy-1-methoxy-1-oxo-phospholane as colorless crystals of melting point 183° C. (recrystallized from propan-2-ol).

$C_7H_{14}ClO_3P$ (212.62)

| calculated: | C 39.55 | H 6.64 | Cl 16.68 | P 14.57 |
|---|---|---|---|---|
| found: | C 39.3 | H 6.6 | Cl 16.7 | P 14.5 |

Evaporating the filtrate at 40° C./1.6×10⁻² bar, stirring the residue with 100 ml of methylene chloride, filtering off the salt which has precipitated and concentrating the filtrate at 30° C./2.0×10⁻² bar gives 53 g (49.8%) of a further isomer of 3-chloro-3,4-dimethyl-4-hydroxy-1-methoxy-1-oxo-phospholane as colorless crystals of melting point 159° C. (recrystallized from acetone).

$C_7H_{14}ClO_3P$ (212.62)

| calculated: | C 39.55 | H 6.64 | Cl 16.68 | P 14.57 |
|---|---|---|---|---|
| found: | C 39.7 | H 6.5 | Cl 16.4 | P 14.6 |

For the formation of two isomeric 3-chloro-4-hydroxy-1-oxo-phospholanes in the process according to the invention, compare also Example 9.

EXAMPLE 20

Analogously to Example 6, 87 g (0.5 mole) of 1-ethoxy-3,4-dimethyl-1-oxo-Δ³-phospholene in 150 ml of water are reacted with 35.5 g (0.5 mole) of chlorine and 26.5 g (0.25 mole) of sodium carbonate in 100 ml of water and the mixture is worked up. Working up gives 103 g (90.9%) of 1-ethoxy-3-chloro-3,4-dimethyl-4-hydroxy-1-oxo-phospholane as colorless crystals of melting point 134° C. (recrystallized from ethyl acetate).

$C_8H_{16}ClO_3P$ (226.64)

| calculated: | C 42.40 | H 7.12 | Cl 15.64 | P 13.67 |
|---|---|---|---|---|

| -continued | | | |
|---|---|---|---|
| found: | C 42.4 H 7.1 | Cl 15.7 | P 13.7 |

I claim:
1. A process for the preparation of a 1-oxo-phospholane-chlorohydrin, which comprises reacting water, a 1-oxo-phospholene, chlorine and a base which bonds hydrogen chloride, the amounts of said phospholene, chlorine and base being a molar ratio of about 1:1:1.

2. A process as claimed in claim 1, wherein the 1-oxo-phospholene is a compound of the formula

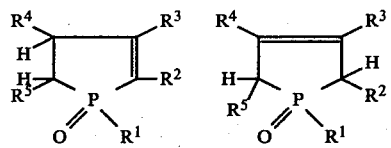

wherein $R^1$ is alkyl of from 1 to 12 carbon atoms, or said alkyl substituted by chlorine, bromine or both, alkoxy of from 1 to 12 carbon atoms, or said alkoxy substituted by chlorine, bromine or both, or a radical selected from the group consisting of cyclopentyl, cyclohexyl, phenyl, naphthyl, cyclopentoxy, cyclohexoxy, phenoxy and naphthoxy, or said radical substituted by alkyl of from 1 to 4 carbon atoms, alkoxy of from 1 to 4 carbon atoms, chlorine, bromine, or a combination thereof, and $R^2$, $R^3$, $R^4$ and $R^5$, independently of one another, are hydrogen, alkyl of from 1 to 4 carbon atoms, alkoxy of from 1 to 4 carbon atoms, phenyl, chlorine or bromine.

3. A process as claimed in claim 2, wherein $R^1$ is alkyl of from 1 to 4 carbon atoms, said alkyl substituted by chlorine, bromine or both, alkoxy of from 1 to 4 carbon atoms, said alkoxy substituted by chlorine, bromine or both or phenyl, $R^2$ and $R^5$ are hydrogen and $R^3$ and $R^4$, independently of one another, are hydrogen or methyl.

4. A process as claimed in claim 1, 2 or 3, wherein the base which bonds with hydrogen chloride is an alkali metal hydroxide, a carbonate, a bicarbonate, ammonia, a lower aliphatic amine, or a combination thereof.

5. A process as claimed in claim 4, wherein water is present in mixture with a water-miscible inert organic solvent selected from the group consisting of lower alcohols, lower aliphatic ketones, water-soluble ethers, and combinations thereof.

6. A process as claimed in claim 1, 2 or 3, wherein reaction is effected in a temperature range of from about −10° to 100° C.

7. A process as claimed in claim 6, wherein reaction is effected in a temperature range of from about 0° to 50° C.

8. A process as claimed in claim 1, 2 or 3, wherein a pH in the range of from about 3 to 9 is maintained during reaction.

9. A process as claimed in claim 1, wherein water is in mixture with a water-miscible inert organic solvent.

* * * * *